United States Patent
Tammen et al.

(10) Patent No.: US 11,737,909 B2
(45) Date of Patent: Aug. 29, 2023

(54) MALE INCONTINENCE DEVICE

(71) Applicant: Melissa Kay Tammen, Fort Worth, TX (US)

(72) Inventors: Melissa Kay Tammen, Fort Worth, TX (US); Rhonda Kay Wright, Weatherford, TX (US)

(73) Assignee: 4 Mankind Inc., Southlake, TX (US)

( * ) Notice: Subject to any disclaimer, the term of this patent is extended or adjusted under 35 U.S.C. 154(b) by 741 days.

(21) Appl. No.: 16/186,108

(22) Filed: Nov. 9, 2018

(65) Prior Publication Data

US 2019/0133814 A1 May 9, 2019

Related U.S. Application Data

(60) Provisional application No. 62/583,725, filed on Nov. 9, 2017.

(51) Int. Cl.
*A61F 5/453* (2006.01)
*A61F 5/44* (2006.01)
(Continued)

(52) U.S. Cl.
CPC ............ *A61F 5/453* (2013.01); *A61F 5/4404* (2013.01); *A61F 13/471* (2013.01); (Continued)

(58) Field of Classification Search
CPC .... A61F 5/453; A61F 13/4915; A61F 5/4404; A61F 13/471; A61F 13/53; A61F 13/58; A61F 5/4408; A61F 13/49
See application file for complete search history.

(56) References Cited

U.S. PATENT DOCUMENTS

| | | |
|---|---|---|
| 3,343,898 A | 9/1967 | Larson |
| D260,046 S | 8/1981 | Burkard |
| (Continued) | | |

FOREIGN PATENT DOCUMENTS

WO   2004071361 A1   8/2004

OTHER PUBLICATIONS

Wikipedia Contributors. (Nov. 30, 2019). Superabsorbent polymer. Wikipedia; Wikimedia Foundation. https://en.wikipedia.org/wiki/Superabsorbent_polymer (Year: 2015).*

(Continued)

*Primary Examiner* — Sarah Al Hashimi
*Assistant Examiner* — Hans Kaliher
(74) *Attorney, Agent, or Firm* — Edwin S. Flores; Chalker Flores, LLP

(57) ABSTRACT

The present invention includes a male incontinence collection container comprising: a walled absorbent cored absorption chamber with an elastic aperture adapted to allow a penis to be in fluid communication with the chamber, wherein the chamber is shaped to deflect urine away from a body during urination, and wherein the elastic aperture is defined further as a breathable, tubular material to aid in the placement and retention in place of the penis; a hydrophobic material positioned between the chamber and the body to prevent contact of the urine with the body; and an absorbent material in the chamber that converts fluid to gel in fluid communication with the chamber, wherein the absorbent material absorbs and retains urine, while keeping a user dry and free from urine contact.

6 Claims, 11 Drawing Sheets

(51) Int. Cl.
  *A61F 13/471* (2006.01)
  *A61F 13/491* (2006.01)
  *A61F 13/53* (2006.01)
  *A61F 13/58* (2006.01)

(52) U.S. Cl.
  CPC .......... *A61F 13/4915* (2013.01); *A61F 13/53* (2013.01); *A61F 13/58* (2013.01)

(56) References Cited

U.S. PATENT DOCUMENTS

| | | | |
|---|---|---|---|
| 4,559,051 A | 12/1985 | Hanson | |
| 4,813,943 A * | 3/1989 | Smith | A61F 5/4408 |
| | | | 604/350 |
| 5,300,052 A | 4/1994 | Kubo | |
| 5,342,332 A | 8/1994 | Wheeler | |
| 5,542,941 A * | 8/1996 | Morita | A61F 13/515 |
| | | | 604/385.04 |
| 5,618,279 A | 4/1997 | Pudlo | |
| 5,776,123 A * | 7/1998 | Goerg | A61F 13/58 |
| | | | 604/389 |
| 5,897,540 A * | 4/1999 | Grundke | A61F 5/453 |
| | | | 604/352 |
| 6,129,718 A | 10/2000 | Wada | |
| 6,338,729 B1 * | 1/2002 | Wada | A61F 13/471 |
| | | | 604/385.01 |
| 6,635,038 B2 | 10/2003 | Scovel | |
| 6,817,992 B1 * | 11/2004 | Sassak | A61F 13/4915 |
| | | | 604/385.09 |
| 7,658,730 B2 | 2/2010 | Conley | |
| D650,477 S | 12/2011 | Morrell-Schwartz | |
| D681,914 S | 5/2013 | Scott | |
| D693,464 S | 11/2013 | Neely | |
| 8,690,849 B2 | 4/2014 | Bach et al. | |
| 8,721,608 B2 | 5/2014 | Bach et al. | |
| 9,271,863 B2 | 3/2016 | Stroebech et al. | |
| D761,520 S | 7/2016 | Klein | |
| D762,045 S | 7/2016 | Popp | |
| 9,572,707 B2 | 2/2017 | Bach et al. | |
| 9,597,428 B2 | 3/2017 | Stroebech et al. | |
| D798,530 S | 10/2017 | Cook | |
| 10,058,463 B2 | 8/2018 | Johnson | |
| D838,931 S | 1/2019 | Yan | |
| D846,833 S | 4/2019 | Cai | |
| D850,059 S | 6/2019 | Cai | |
| D864,521 S | 10/2019 | Benavides | |
| D874,090 S | 2/2020 | Benavides | |
| D876,750 S | 3/2020 | Benavides | |
| D877,453 S | 3/2020 | Benavides | |
| 10,588,793 B2 | 3/2020 | Lumaque-Steeman | |
| 2001/0031933 A1 * | 10/2001 | Cannon | A61F 5/453 |
| | | | 600/580 |
| 2004/0073180 A1 * | 4/2004 | Strannemalm | A61F 13/49001 |
| | | | 604/349 |
| 2006/0224138 A1 | 10/2006 | Heki | |
| 2007/0225670 A1 * | 9/2007 | Connell | A61F 13/4915 |
| | | | 604/385.09 |
| 2007/0243385 A1 | 10/2007 | Evans et al. | |
| 2012/0046633 A1 | 2/2012 | Okawa et al. | |
| 2012/0165768 A1 * | 6/2012 | Sekiyama | A61F 5/453 |
| | | | 604/353 |
| 2012/0310190 A1 | 12/2012 | LaVon et al. | |
| 2013/0041344 A1 | 2/2013 | Proileau et al. | |
| 2013/0090621 A1 * | 4/2013 | Delattre | A61F 13/471 |
| | | | 604/385.01 |
| 2015/0209194 A1 * | 7/2015 | Heyman | A61F 5/453 |
| | | | 604/385.03 |
| 2015/0250656 A1 | 9/2015 | Maksimow | |
| 2015/0320583 A1 * | 11/2015 | Harvie | A61F 5/441 |
| | | | 604/351 |
| 2017/0112657 A1 | 4/2017 | Bach et al. | |
| 2017/0367873 A1 * | 12/2017 | Grannum | A61F 5/4408 |
| 2018/0132538 A1 | 5/2018 | Yan | |
| 2019/0133814 A1 | 5/2019 | Tammen | |

OTHER PUBLICATIONS

PCT/US2018/060130 International Search Report and Written Opinion by the USPTO dated Jan. 22, 2019, 14 pp.

* cited by examiner

MALE INCONTINENCE DEVICE

CROSS-REFERENCE TO RELATED APPLICATIONS

This application claims priority to U.S. Provisional Application Ser. No. 62/583,725 filed Nov. 9, 2017, the entire contents of which are incorporated herein by reference.

STATEMENT OF FEDERALLY FUNDED RESEARCH

None.

TECHNICAL FIELD OF THE INVENTION

The present invention relates in general to the field of devices and methods for urine collection, and more particularly, to a novel pouch or underwear for male incontinence.

BACKGROUND OF THE INVENTION

Without limiting the scope of the invention, its background is described in connection with incontinence.

One such invention is described in U.S. Pat. No. 4,559,051, issued to Hanson and entitled, "Disposable incontinence diaper." This inventor is said to teach a disposable diaper having improved liquid receiving and retaining capabilities. The diaper includes a waterproof barrier formed as a flattened bag and has a single opening located adjacent the perineal area of the body of the wearer. Two layers of filler material are positioned within the barrier bag, and an upper layer is adjacent the opening and is a wicking material, while a lower layer is a superabsorbent material. The invention is said to be useful for both men and women, however, in a male version of the diaper, this inventor is said to teach a pouch that is formed over the opening into which the wearer's penis is inserted to direct voided urine through the bag opening.

Another such invention is taught in U.S. Pat. No. 4,813,943, issued to Smith and entitled, "Urinary incontinence collector." Briefly, this inventor is said to teach a wearable urinary incontinence collector that consists of a pair of bags designed and shaped to be worn on the inside thighs of an individual and strapped to the legs. A frontal web is said to cover the groin area and supports the bags in connection with a suitable array of straps. The arrangement is said to be virtually leak-proof and inconspicuous when worn while standing, sitting, or lying.

Yet another such invention is taught in U.S. Pat. No. 5,342,332, issued to Wheeler and entitled "Male disposable incontinence device." Briefly, this inventor is said to teach a male, disposable, incontinence device, that comprises a generally delta-shaped package that includes an outer, flexible sheet forming a protective container (the sheet defining a front wall and a rear wall), with a penile slit in the rear wall, and absorbent material in the container to overlie the slit, and to absorb urine leaked within the container via the slit.

Yet another such invention is taught in U.S. Pat. No. 5,618,279, issued to Pudlo and entitled, "Medical protection device for males." Briefly, this inventor is said to teach an incontinence garment and protection device that includes a generally planar deflection shield formed of a moisture impervious material. The deflection shield is said to be of sufficient length to extend from above the penis shaft downwardly to the approximate level of the scrotum of the male. The deflection shield can also includes a clearance aperture permitting the penis shaft to extend through the deflection shield to assure urine is deflected away from the scrotum of the male. The deflection shield is said to include a sack-like structure extending from a lower portion of the deflection shield adapted to at least partially enclose the scrotum of the male. In an alternative embodiment, a lower portion of the deflection shield is shown directly attached to the incontinence garment.

Yet another such invention is taught in U.S. Pat. No. 6,338,729, issued to Wada, et al., and entitled "Urine absorbing pad." Briefly, these inventors are said to teach a urine absorbing pad comprising a laminate including: a liquid permeable internal surface sheet; a liquid impermeable external surface sheet; and an absorbent core sandwiched between the internal and external surface sheets. The laminate forming a bag body is said to have an opening, at which opening the internal surface sheet is directed inward, and the opening is positioned closer to an upper end of the bag body than to a lower end of the bag body. The upper end and the lower end are of the bag body extended substantially at a right angle with respect to each other. The opening is said to be formed into a slit shape having a longitudinal direction from the upper end toward the lower and.

Yet another such invention is taught in U.S. Pat. No. 6,635,038, issued to Scovel and entitled "Disposable incontinence device." Briefly, this inventor is said to teach an incontinence device having a disposable urinary bag that includes a plurality of attachment means located on its outside surface for securing the disposable urinary bag to an adjustable attachment belt. Housed within the disposable urinary bag is an absorbent material for urine absorption. The disposable urinary bag has at an upper central region an elastic ring or seal that provides a barrier against urine when a penis is inserted into it. On the top portion of the elastic ring, a slit is said to be provided with a sealing tab and an adhesive to enlarge or constrict the size of the elastic ring. The adjustable attachment belt is said to comprise a portion that fits around the wearer's waist with a plurality of attachment means to secure the upper portion of the disposable urinary bag in conjunction with a plurality of leg straps and to provide a connection means from the adjustable attachment belt to the lower portion of the disposable urinary bag.

Finally, another such invention is taught in U.S. Pat. No. 7,658,730, issued to Conley and entitled "Adult male disposable incontinence system for disposable underwear." Briefly, this inventor is said to teach an external male urine collection device that is inserted into a front opening of a disposable nonwoven diaper or brief. The device is said to include a resilient ring for receiving and restraining the penis in a funnel-shaped collection assembly bag extending from the diaper or brief. Further, a distal funnel-like end of the collection bag is said to be attached to a one-way valve and tube assembly to direct the urine from the bag. In one example, the tube is said to be attached to a bedside urine storage bag or leg bag.

However, despite these many variations in methods for attachment, location for attachment of a pouch, absorbent materials, openings, and bags, there remains a need for a male incontinence device that is easy to manufacture, that is able to reduce or eliminate the conditions that lead to urinary tract infections, and that is comfortable to wear and reduces the profile of the device or pouch to increase the dignity of the wearer. More particularly, a need remains for a simple and effective device that can be adapted for use with existing underwear or that can be customized and assembled using existing equipment and materials into a single-use, disposable male incontinence device.

Thus, a need remains for novel devices and methods for urine collection of male incontinence, with enhanced dignity and fluid retention.

SUMMARY OF THE INVENTION

In one embodiment, the present invention includes a male incontinence collection container comprising: a walled absorbent cored absorption chamber with an elastic aperture adapted to allow a penis to be in fluid communication with the chamber, wherein the chamber is shaped to deflect urine away from a body during urination, and wherein the elastic aperture is defined further as a breathable, tubular material to aid in the placement and retention in place of the penis; a hydrophobic material positioned between the chamber and the body to prevent contact of the urine with the body; and an absorbent material in the chamber that converts fluid to gel in fluid communication with the chamber, wherein the absorbent material absorbs and retains urine, while keeping a user dry and free from urine contact. In one aspect the elastic aperture is defined further as a tubular elasticated and bobbed material that is capable of rolling into the chamber. In another aspect, the elastic aperture is defined further as a tubular elasticated and bobbed material is capable of rolling outwardly from the chamber over a corona of the penis to a neck of the penis. In another aspect, the container further comprises a deflector within the chamber that channels urine into the absorbent material. In another aspect, the elastic aperture is provides for 360 degree retention of a penal fuliculum. In another aspect, the chamber is integral with a brief, wherein the absorbent cellulose material in the chamber, that the chamber is in fluid communication with the absorbent material positioned down a front of a groin and in an area between the legs of the brief to prevent chafing, rash and infections. In another aspect, the container is integral with a brief or boxer and the brief or boxer is disposable. In another aspect, the container is single use. In another aspect, the chamber is made from a non-woven hydrophilic material selected from cellulose, modified-cellulose, linen, cotton, rayon fiber, viscose fiber, cotton fiber, lyocell fiber, or mixtures thereof. In another aspect, the hydrophobic layer comprises polyester/polyethylene terephthalate (PET), polyamide 6 (PA6), polyamide 66 (PA66), nylon 6, nylon 66, polypropylene (PP), or polyolefin, modacrylic or copolymer thereof, a fluoropolymer selected from polytetrafluoroethylene (PTFE), perfluoroalkoxy polymer (PFA), or fluorinated ethylene-propylene (FEP), polypropylene, polyethyleneterephthalate, polybutyleneterephthalate, poly(trimethylene terephthalate), polylactide, nylon, polyacrylonitrile, polybenzimidazole, fluoropolymer, a copolymers thereof, or combination thereof. In another aspect, the hydrophobic layer is channeled toward the chamber. In another aspect, the hydrophobic layer further comprises a channel, groove, or imprinting that channels urine toward the absorbent material in the chamber. In another aspect, the absorbent material comprises polybeads, a hydrogel forming polymer, a polymer comprising saturated one or more amines and/or saturated polyamines selected from (mono, di and poly)aminoalkanes, (mono, di and poly) aminopolyethers, allylamine, alkyl(meth)allylamines, e.g., methyl allylamine, methyl methallylamine, ethyl methallylamine, and ethyl allylamine; methyl-, ethyl-, propyl- and butylamine, diallylamine, dimethallylamine, aniline, ethylenediamine, diethylenetriamine, hexamethylenediamine, trimethylhexamethylenediamine, neopentane diamine, 1,2-propylenediamine, 4,7-dioxadecane-1,10-diamine, 4,9-dioxadodecane-1,12-diamine, polyether diamines, polyalkylene glycol diamines, 3-amino-1-methylaminopropane, bis(3-aminopropyl)methylamine, isophorone diamine, 4,4'-diaminodicyclohexylmethane, 1-(2-aminoethyl)piperazine, o-, m-, or p-phenylenediamine, 4,4'-diaminodiphenyimethane, 1,4-diaminoanthraquinone, 2,4,6-triamino-1,3,5-triazine, aminopyridine, glucosamine, and mixtures thereof. In another aspect, the chamber is shaped to contour around a leg portion of elongated briefs to evenly distribute the liquid through out the chamber to reduce or eliminate bulging of the brief.

In another embodiment, the present invention includes a male incontinence garment comprising: an absorption chamber comprising an elastic aperture adapted to allow a penis to be in fluid communication with the chamber, wherein the chamber is shaped to deflect urine away from a body during urination, wherein the elastic aperture is defined further as a breathable, tubular material to aid in the placement and retention in place of the penis; and an absorbent material in the chamber that converts fluid to gel, wherein the absorbent material absorbs and retains urine, while keeping a user dry and free from urine contact. In one aspect, a hydrophobic material is positioned between the chamber and the body to prevent contact of the urine with the body that is integral with the garment. In another aspect, the elastic aperture is defined further as a tubular elasticated and bobbed material is capable of rolling into the chamber. In another aspect, the elastic aperture is defined further as a tubular elasticated and bobbed material is capable of rolling outwardly from the chamber over a corona of the penis to a neck of the penis. In another aspect, the garment further comprising a deflector within the chamber that channels urine into the absorbent material. In another aspect, the elastic aperture is provides for 360 degree retention of a penal fuliculum. In another aspect, the chamber is integral with a brief, wherein the absorbent cellulose material in the chamber, that the chamber is in fluid communication with the absorbent material positioned down a front of a groin and in an area between the legs of the brief to prevent chafing, rash and infections. In another aspect, the garment is disposable. In another aspect, the garment is single use. In another aspect, the chamber is made from a non-woven hydrophilic material selected from cellulose, modified-cellulose, linen, cotton, rayon fiber, viscose fiber, cotton fiber, lyocell fiber, or mixtures thereof. In another aspect, the hydrophobic layer comprises polyester/polyethylene terephthalate (PET), polyamide 6 (PA6), polyamide 66 (PA66), nylon 6, nylon 66, polypropylene (PP), or polyolefin, modacrylic or copolymer thereof, a fluoropolymer selected from polytetrafluoroethylene (PTFE), perfluoroalkoxy polymer (PFA), or fluorinated ethylene-propylene (FEP), polypropylene, polyethyleneterephthalate, polybutyleneterephthalate, poly(trimethylene terephthalate), polylactide, nylon, polyacrylonitrile, polybenzimidazole, fluoropolymer, a copolymers thereof, or combination thereof. In another aspect, the hydrophobic layer further comprises a channel, groove, or imprinting that channels urine toward the absorbent material in the chamber. In another aspect, the garment further comprises a chamber positioned in front of a groin and under legs to prevent chafing, rash and infections. In another aspect, the absorbent material comprises polybeads, a hydrogel forming polymer, a polymer comprising saturated one or more amines and/or saturated polyamines selected from (mono, di and poly)aminoalkanes, (mono, di and poly)aminopolyethers, allylamine, alkyl(meth)allylamines, e.g., methyl allylamine, methyl methallylamine, ethyl methallylamine, and ethyl allylamine;

methyl-, ethyl-, propyl- and butylamine, diallylamine, dimethallylamine, aniline, ethylenediamine, diethylenetriamine, hexamethylenediamine, trimethylhexamethylenediamine, neopentane diamine, 1,2-propylenediamine, 4,7-dioxadecane-1,10-diamine, 4,9-dioxadodecane-1,12-diamine, polyether diamines, polyalkylene glycol diamines, 3-amino-1-methylaminopropane, bis(3-aminopropyl)methylamine, isophorone diamine, 4,4'-diaminodicyclohexylmethane, 1-(2-aminoethyl)piperazine, o-, m-, or p-phenylenediamine, 4,4'-diaminodiphenyimethane, 1,4-diaminoanthraquinone, 2,4,6-triamino-1,3,5-triazine, aminopyridine, glucosamine, and mixtures thereof. In another aspect, the chamber is shaped to contour around a leg portion of elongated briefs to evenly distribute the liquid through out the chamber to reduce or eliminate bulging of the brief.

In another embodiment, the present invention includes a method for male urine collection comprising: fitting a male with a urine collection device that comprises: a double-walled absorbent cored absorption chamber with an elastic aperture adapted to allow a penis to be in fluid communication with the chamber, wherein the chamber is shaped to deflect urine away from a body during urination, and wherein the elastic aperture is defined further as a breathable tubular material to aid in the placement and retention in place of the penis; a hydrophobic material positioned between the chamber and the body to prevent contact of the urine with the body; and an absorbent material in the chamber that converts fluid to gel in fluid communication with the chamber, wherein the absorbent material absorbs and retains the male urine, while keeping a user dry and free from urine contact; and retaining the penis with the breathable tubular material, wherein a penis head is exposed to the interior of the chamber but tubular material is capable of expanding and contracting with a size of the penis head and reduces exposure to possible infection. In one aspect, the elastic aperture is defined further as a tubular elasticated and bobbed material is capable of rolling into the chamber. In another aspect, the elastic aperture is defined further as a tubular elasticated and bobbed material is capable of rolling outwardly from the chamber over a corona of the penis to a neck of the penis. In another aspect, the method further comprises positioning a urine deflector within the chamber that channels urine into the absorbent material. In another aspect, the elastic aperture is provides for 360 degree retention of a penal fuliculum. In another aspect, the chamber is integral with a brief, wherein the absorbent cellulose material in the chamber, that the chamber is in fluid communication with the absorbent material positioned down a front of a groin and in an area between the legs of the brief to prevent chafing, rash and infections. In another aspect, the container is integral with a brief or boxer and the brief or boxer is disposable. In another aspect, the container is single use.

In another embodiment, the present invention includes a method male urine collection comprising: providing a male with a double-walled absorbent cored absorption chamber with an elastic aperture adapted to allow a penis to be in fluid communication with the chamber, wherein the chamber is shaped to deflect urine away from a body during urination, and wherein the elastic aperture is defined further as a breathable tubular material to aid in the placement and retention in place of the penis, wherein the chamber comprises a urine absorbing material in the chamber; and retaining the penis with the breathable tubular material, wherein a penis head is exposed to the interior of the chamber but tubular material is capable of expanding and contracting with a size of the penis head and reduces exposure to possible infection while keeping a user dry and free from urine contact.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1A:
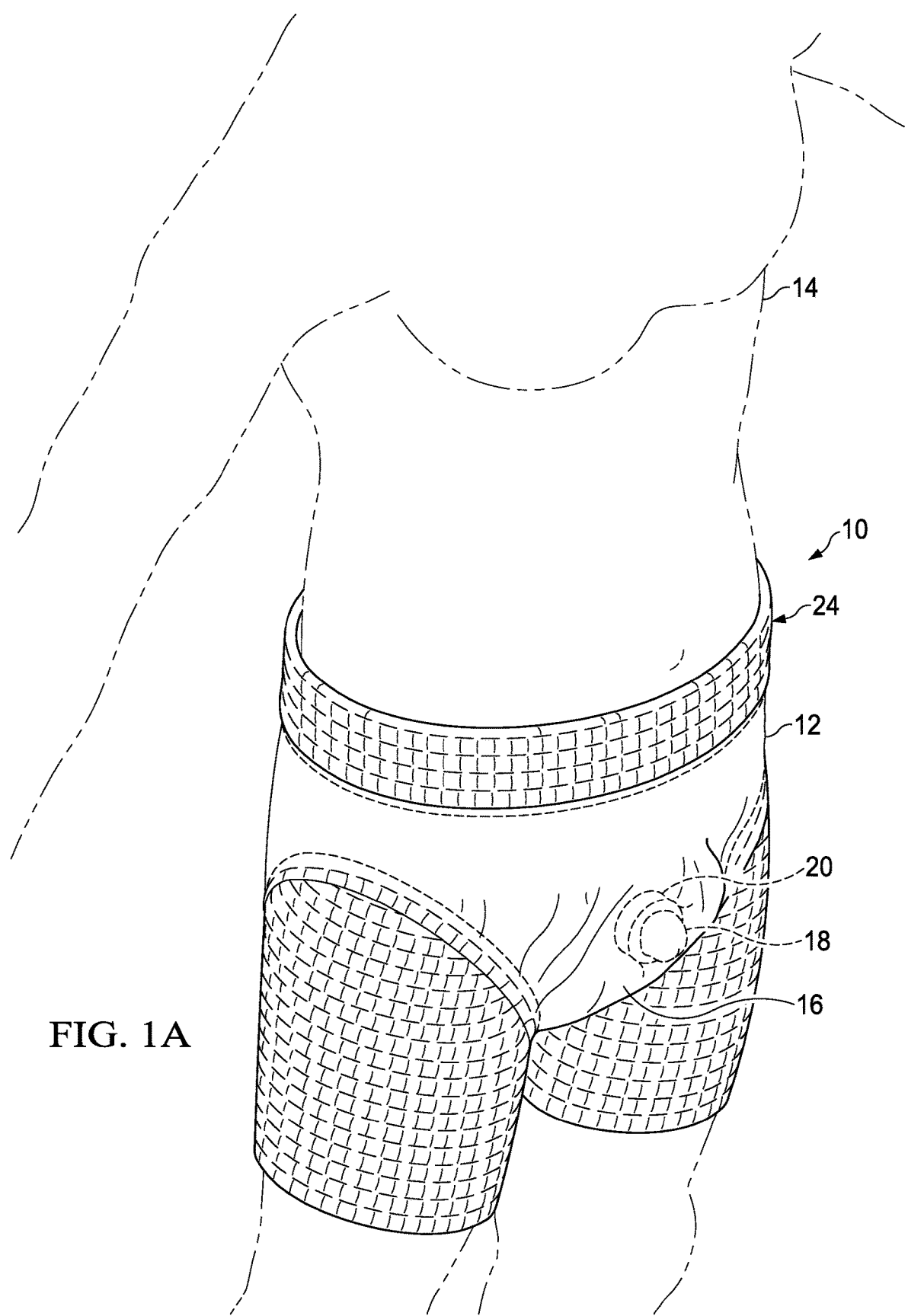
FIG. 1A is an isometric view of an integrated urine collection and male incontinence diaper of the present invention that is integral with a boxer.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

As used herein, the term "hydrophilic" refers to a material having a strong affinity for or the ability to absorb water.

As used herein, the term "hydrophobic" refers to a material lacking an affinity for or the ability to absorb water.

As used herein, the phrases "breathable, tubular material" and "at least partially water tight" refers to a device, such as a elasticated sleeve that can be, e.g., stamped, grooved, striated, elasticated, porous, permeable, semi-permeable, stitched, and/or bobbed, such that it permits some liquid or gas to traverse from the outside environment into and out of the chamber comprising the absorbent material, but that is still somewhat or mostly water tight. Non-limiting examples of the amount of water-tightness can be 75, 80, 85, 90, 91, 92, 93, 94, 95, 96, 97, 98, 99, 99.1, 99.2, 99.3, 99.4, 99.5, 99.6, 99.7, 99.8, or even 99.9% watertight. In one embodiment of the present invention an elasticated, bobbed sleeve is "turtle-neck" shaped and adapted to expand with and contract with the size of a penis, such that urine can be captured by a urine absorbing material, but the elasticated, bobbed sleeve is not so tight that it limits circulation to the penis or that is watertight, like a condom (but not water-tight like a condom), which can cause an increase in urinary tract infections. As such, the present invention includes an at least partially water-tight or "breathable" (but not completely water-tight or water-impermeable structure or material) that can be rolled onto a penis, or the penis can be inserted into, to capture the penis head such that urine from the penis is ducted towards a liquid absorbing material. In one specific example, the breathable, tubular material is not a "condom", "condom-like" or "water-tight". The material can be any of a wide variety of hydrophobic membranes, however, the stamped, grooved, striated, elasticated, porous, permeable, semi-permeable, stitched, and/or bobbed, or other imprinting or distress of the hydrophobic membrane causes it to be at least partially least partially water-tight or "breathable". This least partially water-tight or "breathable" feature prevents the growth of microbes that are obligate anaerobic and partially obligate anaerobic. It also reduces the moisture and other environmental conditions that lead to bacterial growth and urinary tract infections. In certain embodiments, the breathable, tubular material is made from a single layer, a double layer, one or more layers that may be formed during rolling, and will generally be designed to comfortably fit about the corona of the penis.

One non-limiting example of a material that provides the "at least partially water tight" or "breathable, tubular material" sleeve of stamped, grooved, striated, elasticated, porous, permeable, semi-permeable, stitched, and/or bobbed, includes "synthetic material or synthetic fibers" that are formed into a sheet that is then bobbed to form a sleeve. As used herein, the terms "synthetic material" or "synthetic fibers" refers to materials that are synthesized from monomers or multimers and that form polymers. Non-limiting examples of synthetic materials for use with the present invention include, for example, polyester, acrylic, polyamide, polyolefin, polyaramid, polyurethane, regenerated cellulose (i.e., rayon), and blends thereof. The term "polyamide" is intended to describe any long-chain polymer having recurring amide groups (—NH—CO—) as an integral part of the polymer chain. Examples of polyamides include nylon 6; nylon 6, 6; nylon 1, 1; and nylon 6, 10. The term "polyester" is intended to describe any long-chain polymer having recurring ester groups (—C(O)—O—). Examples of polyesters include aromatic polyesters, such as polyethylene terephthalate (PET), polybutylene terephthalate (PBT), polytrimethylene terephthalate (PTT), and polytriphenylene terephthalate, and aliphatic polyesters, such as polylactic acid (PLA). "Polyolefin" includes, for example, polypropylene, polyethylene, and combinations thereof. "Polyaramid" includes, for example, poly-p-phenyleneteraphthalamid (i.e., KEVLAR®), poly-m-phenyleneteraphthalamid (i.e., NOMEX®), and combinations thereof. Natural fibers include, for example, wool, cotton, flax, and blends thereof.

The present invention can also use natural fibers that have been processed and treated to form smaller polymers, oligomers, multimers, fibers, etc., such a cellulose or cellulose derivatives, from, e.g., cotton or bamboo, and that are used with the present invention.

The male incontinence brief is a disposable single-use product designed to absorb and retain urine, while keeping the user dry and free from urine contact. Generally, the separate pouch or device, or the pouch or device that is an integral part of a brief or boxer garment will include one or more of the following:

1. It can include a double walled (back sheet and top sheet), absorbent cored absorption chamber with an elasticated aperture which allows the user's penis to extend into the chamber to assure urine is deflected away from the user's body;

2. It can include a tubular material extends, e.g., stamped, imprinted, elasticated, bobbed, grooved, striated, to connect the exterior environment to the chamber aperture to aid in the placement and retention in place of the penis, while being comfortable, mostly but not completely water-tight, and reducing the possibility of infection;

3. It can be made from absorbent cellulose material with polybeads, which convert fluid to gel;

4. It can include a non-woven hydrophilic material; and/or

5. It can be formed into a men's brief style with chamber running down front of groin and down under legs to prevent chafing, rash and infections.

The Problem: Urinary Caused Infections, Rashes and other Maladies in Incontinent Males.

Long-term care (LTC) patients are at risk of urinary tract infection because of frequent hospital stays, advanced age, exposure to multiple courses of antibiotics and numerous co-morbidities. Older adults have a diminished immune response while the usefulness of antibiotics is decreased due to antibiotic resistant organisms. In addition, many LTC patients deal with cognitive impairment; may not be compliant with personal hygiene and hand washing; have functional impairment that leads to immobility; and suffer from urinary and fecal incontinence. Functional limitations of movement have a circular relationship with infection susceptibility: poor function predisposes older adults to infections and infections, in turn, lead to further functional disability.

Infections in the LTC population have been associated with high rates of morbidity and mortality, extended and recurring hospital stays and substantial healthcare expenses. Risk factors that predispose older adults to infections include the presence of indwelling devices such as urinary catheters. LTC patients with urinary catheters are more prone to urinary tract infections (UTIs), bacteremia and septicemia. Strausbaugh L, Joseph C. The burden of infection in long-term care. Infect. Control Hosp. Epidemiol. 2000; 21:674-679.

Precise estimates on the prevalence and incidence of infections in LTC patients are difficult to obtain due to a remarkable diversity in those being cared for in this setting. A 2004 Nursing Home Survey reported prevalence rate of 5.7% for urinary tract infections in LTC patients older than the age of 65 years. Smith P, Bennett G, Bradley S, et al. SHEA/APIC guideline: infection prevention and control in the long-term care facility. Infect. Control Hosp. Epidemiol. 2008; 29:785-814. In a study to evaluate attributable rates of infections in LTC patients with indwelling devices such as catheter, the incidence rate of all infections among patients with either a feeding tube or a urinary catheter was 331 infections/1000 resident-months or 11.03 infections/1000 resident-days. The incidence rate of infections in non-device patients was substantially lower at 171 infections/1000 resident-months or 5.7 infections/1000 resident-days, with a relative risk of 1.9 (95% CI: 1.4-2.6). Wang L, Lansing B, Symons K, et al. Attributable rates of infections due to indwelling device use in skilled nursing facilities. Presented at: SHEA 2011 Annual Scientific Meeting; Dallas, Tex., USA. 2011. Apr. 1-4, (Abstract 410). A team from New York City's Columbia University School of Nursing surveyed 955 nursing homes in 2014. The researchers also analyzed data from the Centers for Medicare and Medicaid Services. They found that in any given month, for over 88,000 nursing home patients in the study, an average of 5.4 percent of them— more than 4,700 people—had suffered a urinary tract infection. Donna Armellino, R.N., vice president, infection prevention, Northwell Health, Lake Success, N.Y.; Paula Lester, M.D., geriatric medicine, Winthrop-University Hospital, Mineola, N.Y.; Association for Professionals in Infection Control and Epidemiology, news release, Jun. 10, 2016.

Urinary tract is the most common infection in the LTC patient setting. The presence of an indwelling urinary catheter increases the risk of both UTIs and bacteriuria. For example, approximately 3-7% of LTC patients with an indwelling urinary catheter will acquire a UTI with each day the catheter remains in place. By day 30 following catheter insertion, the prevalence of bacteriuria is almost 100%. Warren J, Tenney J, Hoops J, et al. J. Infect. Dis. 1982; 146:719-723. It is estimated that 50% of LTC patients with a urinary catheter will have symptomatic catheter-related urinary tracts infections. Kunin C, Douthitt S, Dancing J, et al. Am. J. Epidemiol. 1992; 135:291-301. In addition, patients with urinary catheters for longer than 30 days have a mortality rate higher than patients without a catheter. The data shows that patients with indwelling urinary catheters have an incidence rate of 9.1 UTIs/1000 resident-days, significantly higher than 2.8 UTIs/1000 resident-days in the nondevice group. Wang L, Lansing B, Symons K, et al. Attributable rates of infections due to indwelling device use in skilled nursing facilities. Presented at: SHEA 2011 Annual Scientific Meeting; Dallas, Tex., USA. 2011. Apr. 1-4, (Abstract 410).

Wide discrepancies remain between research-proven recommendations pertaining to urinary catheter care and health care providers' knowledge. In a study analyzing urinary catheter care knowledge, researchers found a significant and unfortunate disparity between research-proven recommendations and health care provider knowledge: 25% of respondents were unaware of indications for long-term catheter use, 55% were unaware of recommended practices to maintain a closed drainage system, and 70% were unaware of current recommendations against the practice of routine bladder irrigation. Mody L, Saint S, Galecki A, et al. Knowledge of evidence-based urinary catheter care practice recommendations among healthcare workers in nursing homes. J. Am. Geriatr. Soc. 2010; 58:1532-1537.

Scope of the Problem: Widespread and Increasing as the General Population Ages. In 2014, about 67,000 paid, regulated long-term care service providers served about nine million people in the United States. LTC patient services were provided at 4,800 adult day services centers, 12,400 home health agencies 4,000 hospices, 15,600 nursing homes, and 30,200 assisted living and similar residential care communities. CDC, Vital and Health Statistics, Long-Term Care Providers and Services Users in the United States: Data From the National Study of Long-Term Care Providers, 2013-2014, Series 3, Number 38, February 2016. It is estimated that the number of people who will require Nursing home care in the USA will reach 5.3 million by 2030. Knickman J, Snell E. The 2030 problem: caring for aging baby boomers. Health Serv. Res. 2002; 37:849-884. Home health care has expanded in scope and intensity in the United States in the past decade; however infection surveillance, prevention, and control efforts have lagged behind. Prevention and control efforts are largely based upon acute-care practices, many of which are impractical and expensive in a home setting.

An impetus for the present invention was the loss of a patient and friend due an incurable urinary tract infection resulting from incontinence. The patient suffered severe pain from the infection, but also from concomitant ailments. All the adult diapers offered were ill fitting, provided very poor containment and offered little to no absorption. The patient purchased and used additional absorbent pads. Of all the products purchased, none were found to be sufficient to meet the needs.

The patient was in the hospital at least once, if not twice, a week due to on-going illness and the unbearable pain the patient was suffering. The hospital would administer heavy doses of antibiotics and send the patient home with a prescription antibiotic and a pick-line. However, the infections persisted. The patient's body could not remediate the infection if it was still being exposed to the uric acid in which the bacteria lives and passes through. The patient died from urosepsis.

FIG. 1A is an isometric view of an integrated urine collection and male incontinence device 10 of the present invention that is integral with a boxer or garment 12, which is depicted in the form of a diaper that is integral with the boxer or garment 12. A male user 14 is depicted wearing the boxer or garment 12 and a urine collection pouch 16 is depicted in relation to the penis 18 and a breathable, tubular material 20 (in this embodiment shown as an elasticated and bobbed breathable, tubular material) that aid in the placement and retention of the penis 18. Generally, the breathable, tubular material 20 in this embodiment is made from the same material and at the same time as the boxer or garment 12, which is generally a hydrophobic material that is biocompatible and can include embedded within the fabric elastic. The bobbing or weaving 24 is depicted as being found throughout the boxer or garment 12, and missing in some portions, however, the integrated urine collection and male incontinence device 10 is part of the boxer or garment 12. Generally, the user will connect the penis to the integrated urine collection and male incontinence device 10 at the breathable, tubular material 20, as the user pulls-on the boxer or garment 12 over the integrated urine collection and male incontinence device 10. The integrated urine collection and male incontinence device 10 is shaped and integral with the boxer or garment 12 and the male user 14 without the need for an adhesive or fastener. In certain embodiments, the boxer or garment 12 can be modified to have an interlocking shape with the integrated urine collection and male incontinence device 10. The integrated urine collection and male incontinence device 10 can be made from a pliable material that contours to the shape of the male user 14, specifically, in the area around the penis, along the perineum, toward the posterior of the male user 14 (e.g., along the buttocks), or even along the inside of the thighs.

Figure 1B:
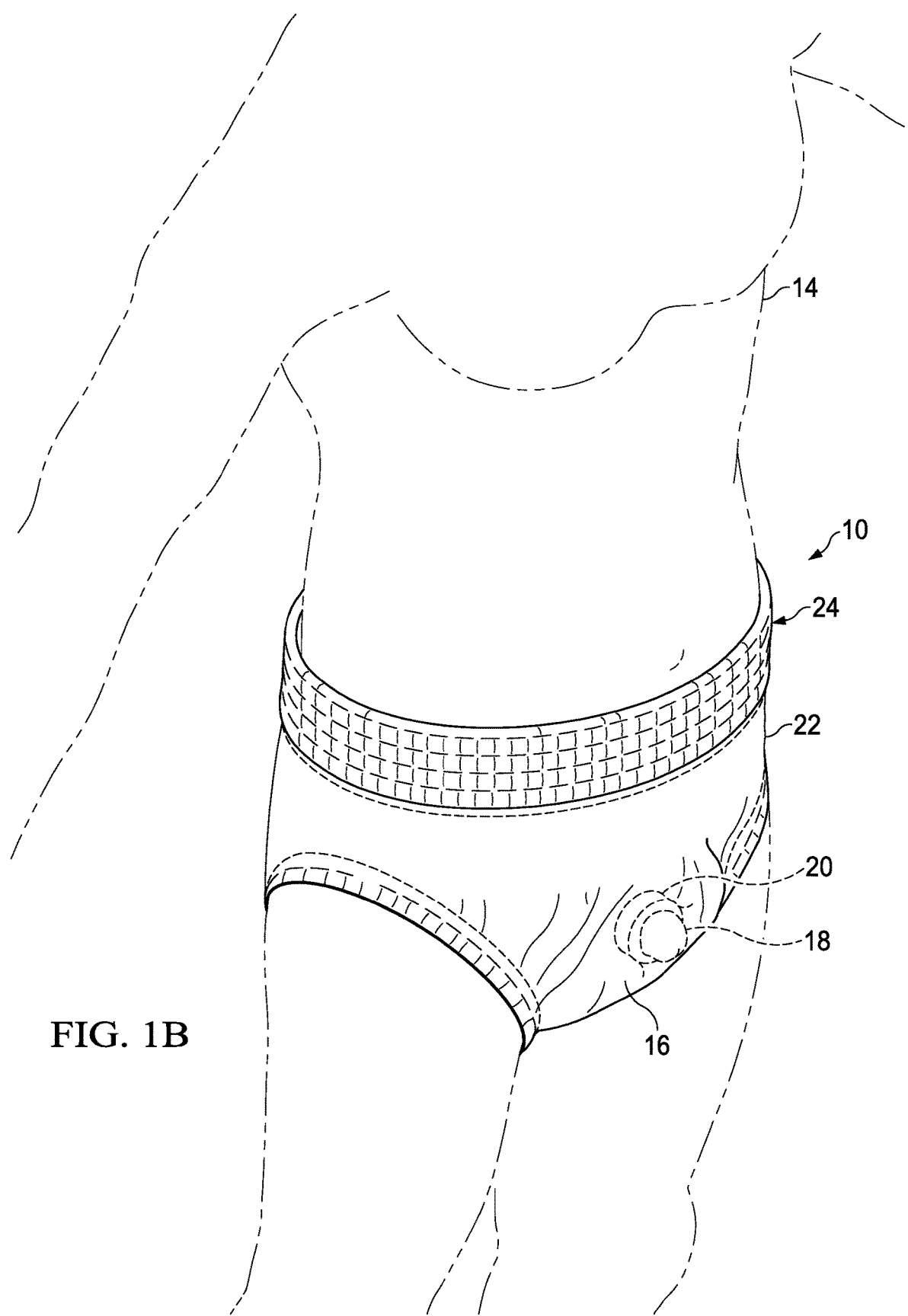
FIG. 1B is an isometric view of an integrated urine collection and male incontinence diaper of the present invention that is integral with a brief.

FIG. 1B is an isometric view of an integrated urine collection and male incontinence device 10 of the present invention that is integral with a brief or garment 22, which is depicted in the form of a diaper that is integral with the boxer or garment 12. A male user 14 is depicted wearing the brief or garment 22 and a urine collection pouch 16 is depicted in relation to the penis 18 and a breathable, tubular material 20 that aid in the placement and retention of the penis 18. Generally, the breathable, tubular material 20 in this embodiment is made from the same material and at the same time as the brief or garment 22, which is generally a hydrophobic material that is biocompatible and can include embedded within the fabric elastic. The bobbing or weaving 24 is depicted as being found throughout the brief or garment 22, and missing in some portions, however, the integrated urine collection and male incontinence device 10 is an integral part of the brief or garment 22. Generally, the user will connect the penis to the integrated urine collection and male incontinence device 10 at the breathable, tubular material 20, as the user pulls-on the brief or garment 22 over the integrated urine collection and male incontinence device 10. The integrated urine collection and male incontinence device 10 is shaped and integral with the brief or garment 22. In certain embodiments, the brief or garment 22 is modified to have an interlocking shape with the integrated urine collection and male incontinence device 10. The integrated urine collection and male incontinence device 10 can be made from a pliable material that contours to the shape of the male user 14, specifically, in the area around the penis, along the perineum, toward the posterior of the male user 14 (e.g., along the buttocks), or even along the inside of the thighs.

Figure 1C:
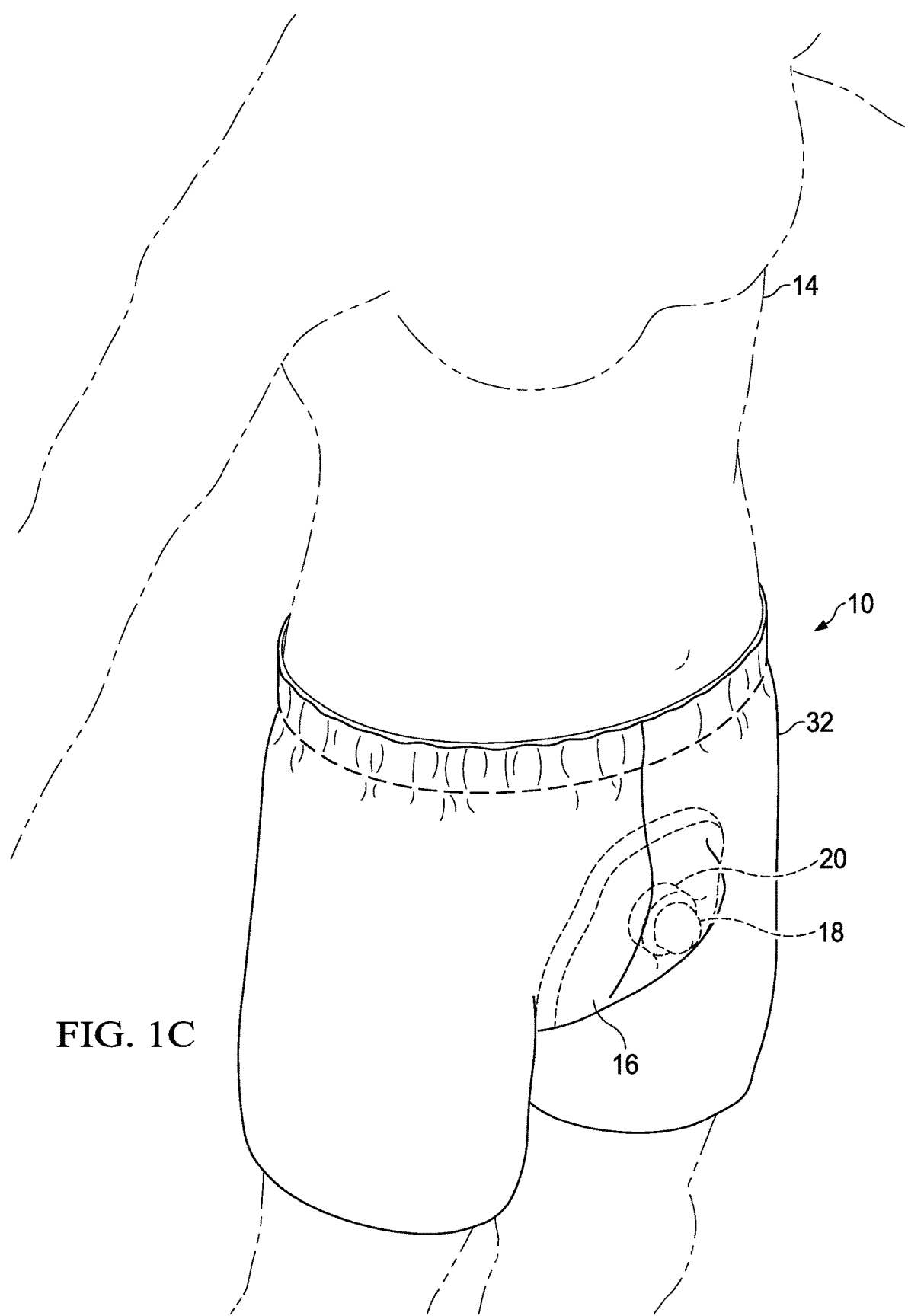
FIG. 1C is an isometric view of the urine collection and male incontinence device of the present invention that is used with an existing boxer underwear.

FIG. 1C is an isometric view of an integrated urine collection and male incontinence device 10 of the present invention and a boxer or garment 32. A male user 14 is depicted wearing the boxer or garment 32 and a urine collection pouch 16 is depicted in relation to the penis 18 and a breathable, tubular material 20 that aid in the placement and retention of the penis 18. Generally, the breathable, tubular material 20 in this embodiment is made from a hydrophobic material that is biocompatible and often elastic. The integrated urine collection and male incontinence device 10 of the present invention can be used with any boxer or garment 32, because in this embodiment the boxer or garment 32 is a standard boxer or garment 32 that can be cotton or other materials, and the integrated urine collection and male incontinence device 10 is inserted into the boxer or garment 32 as a standalone device. Generally, the user will connect the penis to the integrated urine collection and male incontinence device 10 at the breathable, tubular material 20, and can then pull on the boxer or garment 32 over the integrated urine collection and male incontinence device 10. In some instances, it may be preferable to place an adhesive or fastener between the integrated urine collection and male incontinence device 10 and the boxer or garment 32 to reduce movement of the integrated urine collection and male incontinence device 10 with regard to the body of the male user 14. However, the integrated urine collection and male incontinence device 10 is shaped and restrained between the boxer or garment 32 and the male user 14 without the need for an adhesive or fastener. In certain embodiments, the boxer or garment 32 can be modified to have an interlocking shape with the integrated urine collection and male incontinence device 10. The integrated urine collection and male incontinence device 10 can be made from a pliable material that contours to the shape of the male user 14, specifically, in the area around the penis, along the perineum, toward the posterior of the male user 14 (e.g., along the buttocks), or even along the inside of the thighs.

Figure 1D:
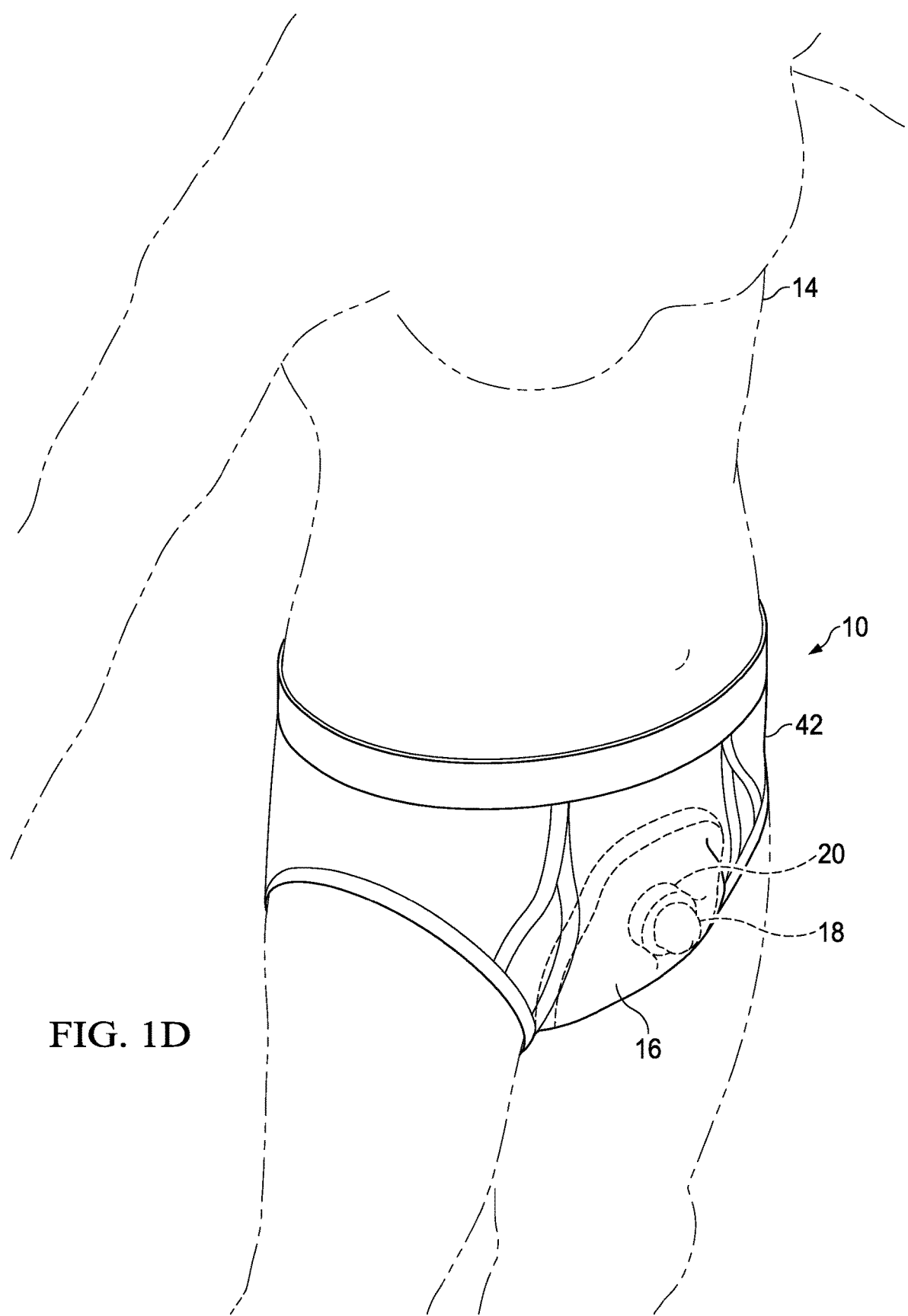
FIG. 1D is an isometric view of the urine collection and male incontinence device of the present invention that is used with an existing brief underwear.

FIG. 1D is an isometric view of an integrated urine collection and male incontinence device 10 of the present invention and a brief or garment 42. A male user 14 is depicted wearing the brief or garment 42 and a urine collection pouch 16 is depicted in relation to the penis 18 and a breathable, tubular material 20 that aid in the placement and retention of the penis 18. Generally, the breathable, tubular elasticated and bobbed material 20 in this embodiment is made from a hydrophobic material that is biocompatible and often elastic. The integrated urine collection and male incontinence device 10 of the present invention can be used with any brief or garment 42, because in this embodiment, the brief or garment 42 is a standard brief or garment 42 that can be cotton or other materials, and the integrated urine collection and male incontinence device 10 is inserted into the brief or garment 42 as a standalone device. Generally, the user will connect the penis to the integrated urine collection and male incontinence device 10 at the breathable, tubular elasticated and bobbed material 20, and can then pull on the brief or garment 42 over the integrated urine collection and male incontinence device 10. In some instances, it may be preferable to place an adhesive or fastener between the integrated urine collection and male incontinence device 10 and the brief or garment 42 to reduce movement of the integrated urine collection and male incontinence device 10 with regard to the body of the male user 14. However, the integrated urine collection and male incontinence device 10 is shaped and restrained between the brief or garment 42 and the male user 14 without the need for an adhesive or fastener. In certain embodiments, the brief or garment 42 can be modified to have an interlocking shape with the integrated urine collection and male incontinence device 10. The integrated urine collection and male incontinence device 10 can be made from a pliable material that contours to the shape of the male user 14, specifically, in the area around the penis, along the perineum, toward the posterior of the male user 14 (e.g., along the buttocks), or even along the inside of the thighs.

Figure 2A:
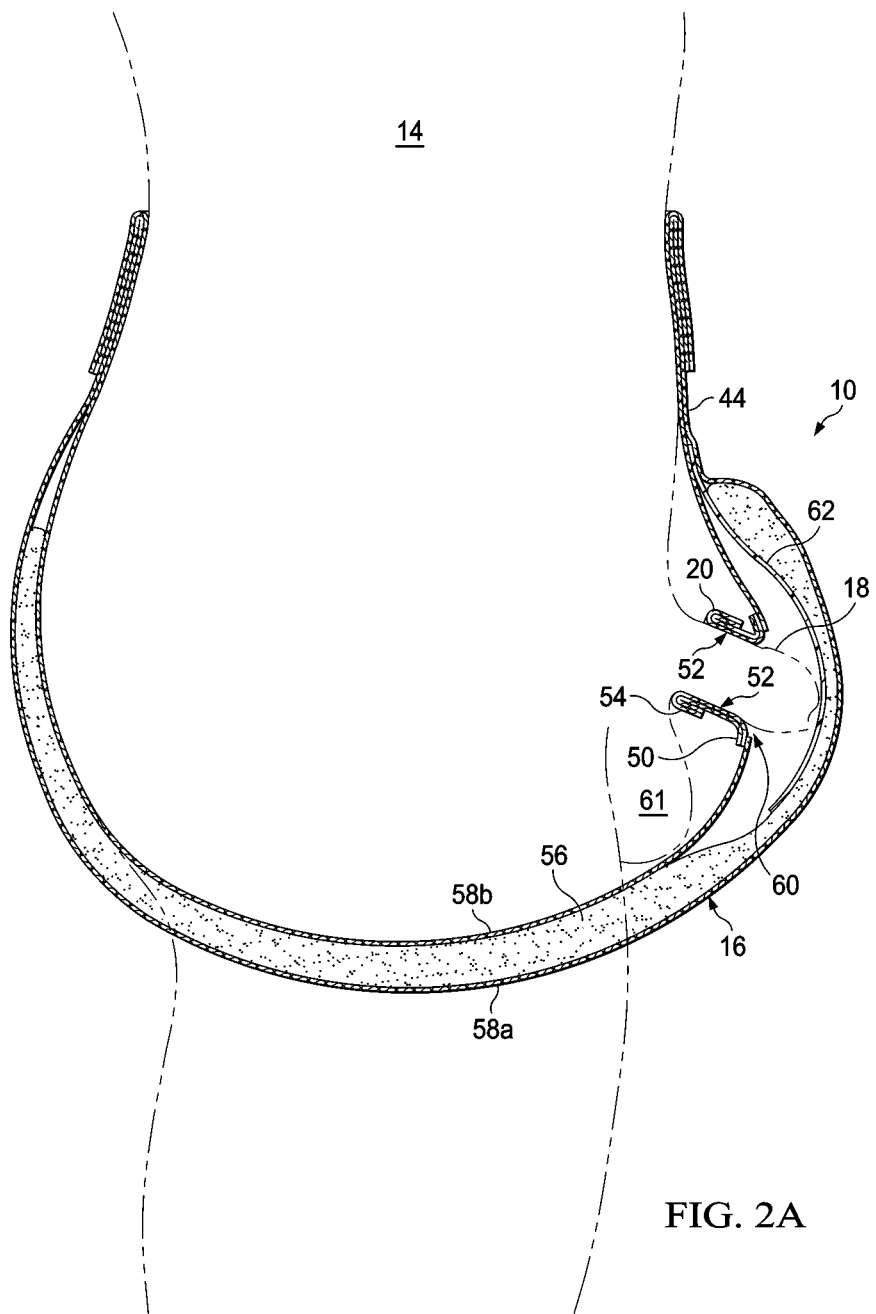
FIG. 2A is a detailed cross-sectional side view of the integrated urine collection and male incontinence device of the present invention integral with a brief, with a breathable, tubular material and showing the details of an inward or distal configuration.

FIG. 2A is a detailed cross-sectional side view of the integrated urine collection and male incontinence device 10 of the present invention integral with a brief 44, with a breathable, tubular material 20 and showing the details of an inward or distal configuration. A male user 14 is depicted wearing the brief 44 and a urine collection pouch 16 is depicted in relation to the penis 18 and a breathable, tubular material 20 that aid in the placement and retention of the penis 18. In this configuration, that breathable, tubular material 20 is depicted as being attached to the brief 44, and having a point of attachment 50, and central portion 52 that is generally cylindrical in shape to adapt to the shaft of the penis 18, and a terminal portion 54 that is depicted as having a double layer of material, in this case the same material as the brief 44, with which it is integral. The breathable, tubular elasticated and bobbed material 20 does not need to be made separately and attached to the brief 20, but can also be made completely or partially integral with the brief 44. The pouch 16 is depicted having an absorbent material 56, which is within hydrophobic and watertight layers 58a and 58b. In operation, the breathable, tubular material 20 is first positioned in a rolled-up configuration, the penis head 18 is inserted into the opening 60 of the pouch 16, and the breathable, tubular material 20 can be rolled-on to the penis shaft. The pouch 16 will generally be shaped or elasticated to take into account the location of the testicles 61 to increase comfort during use of the brief 44. In this figure, the absorbent material 56 is shown both above, in-front of, and below the penis 18, between the legs and even upwardly and behind the buttocks. Also depicted is a channel or deflector 62, that directs the urine away from the penis and toward the absorbent material 56.

Figure 2B:
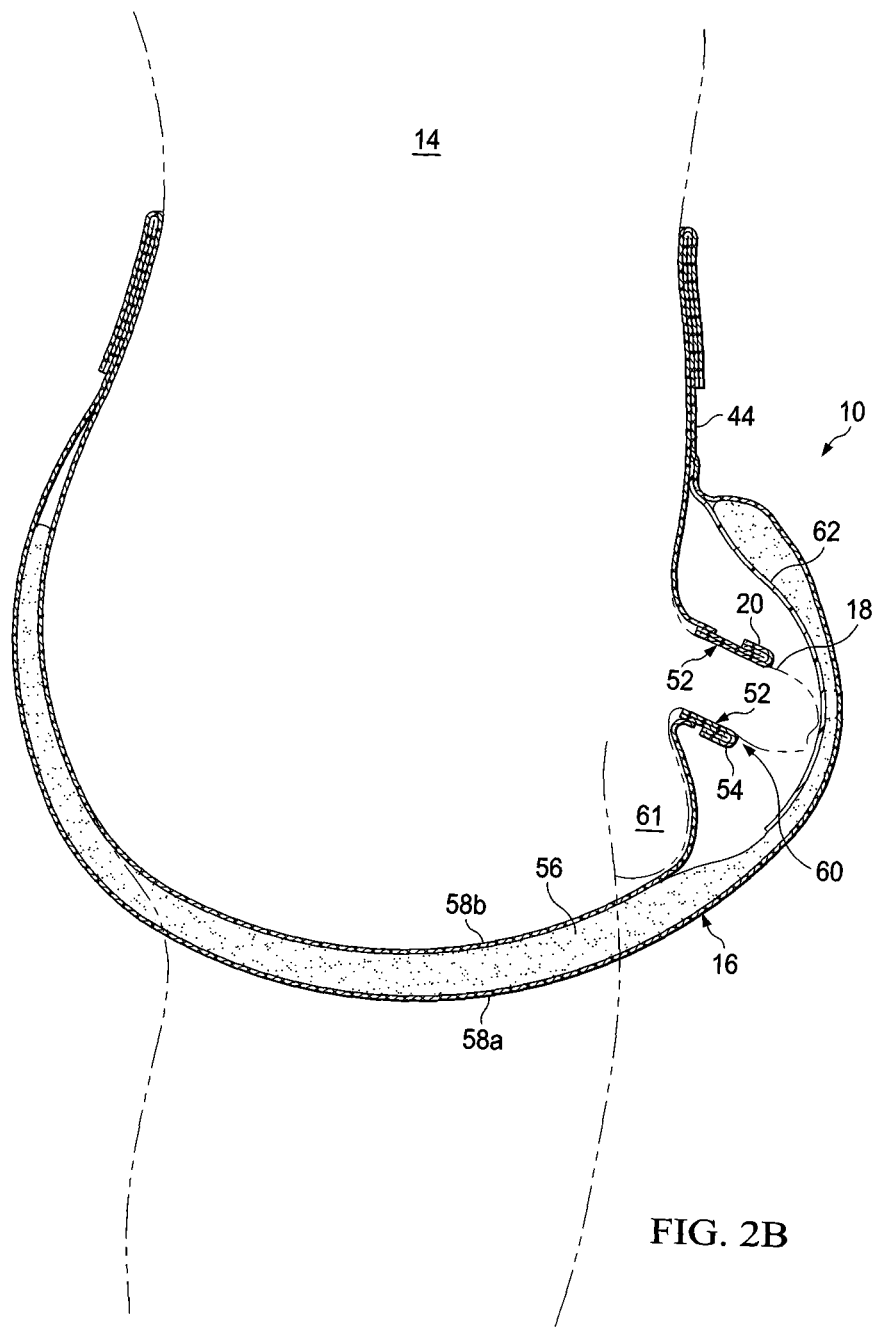
FIG. 2B is a detailed cross-sectional side view of the integrated urine collection and male incontinence device of the present invention integral with a brief, with a breathable, tubular material and showing the details of an outward or proximal configuration.

FIG. 2B is a detailed cross-sectional side view of the integrated urine collection and male incontinence device 10 of the present invention integral with a brief 12, with a breathable, tubular material 20 and showing the details of an outward or proximal configuration. A male user 14 is depicted wearing the boxer or garment 12 and a urine collection pouch 16 is depicted in relation to the penis 18 and a breathable, tubular material 20 that aid in the placement and retention of the penis 18. In this configuration, that breathable, tubular material 20 is depicted as being attached to the brief 44, and having a point of attachment 50, and central portion 52 that is generally cylindrical in shape to adapt to the shaft of the penis 18, and a terminal portion 54 that is depicted as having a double layer of material, in this case the same material as the brief 44, with which it is integral. The breathable, tubular material 20 does not need to be made separately and attached to the brief 20, but can also be made completely or partially integral with the brief 44. The pouch 16 is depicted having an absorbent material 56, which is within hydrophobic and watertight layers 58a and 58b. In operation, the breathable, tubular material 20 is first positioned in a rolled-up configuration, the penis head 18 is inserted into the opening 60 of the pouch 16, and the breathable, tubular material 20 can be rolled-on to the penis shaft. The pouch 16 will generally be shaped or elasticated to take into account the location of the testicles 61 to increase comfort during use of the brief 44. In this configuration the penis 18 is slipped into the opening 60 and the shaft of the penis 18 is in contact with the central portion 52 of the breathable, tubular material 20. In this figure, the absorbent material 56 is shown both above, in-front of, and below the penis 18, between the legs and even upwardly and behind the buttocks. Also depicted is a channel or deflector 62, that directs the urine away from the penis and toward the absorbent material 56.

Figure 2C:
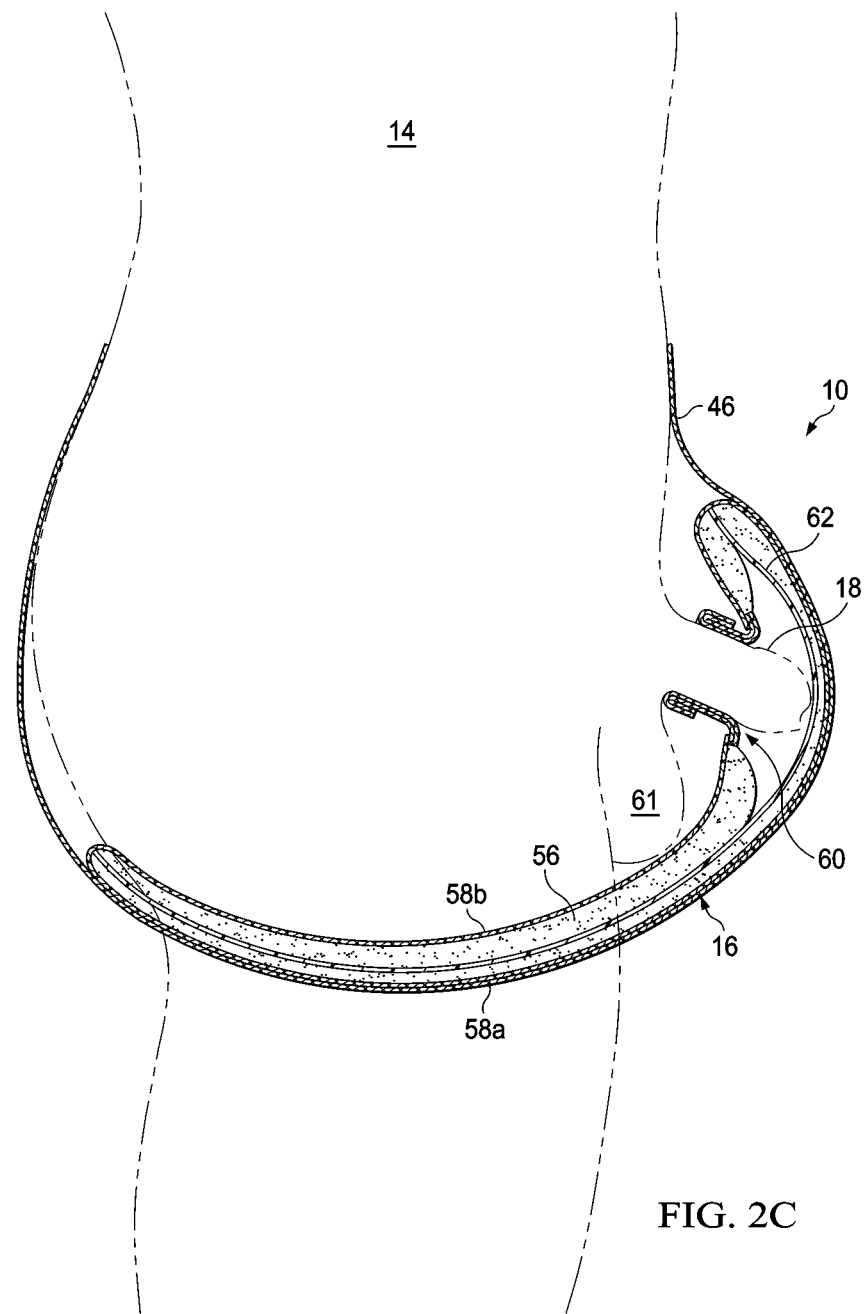
FIG. 2C is a detailed cross-sectional side view of the urine collection and male incontinence device of the present invention used in conjunction with a brief underwear with an inward or distal configuration.

FIG. 2C is a detailed cross-sectional side view of the urine collection and male incontinence device of the present invention used in conjunction with a brief underwear 46 with an inward or distal configuration. The breathable, tubular material 20 is shown with the details of an inward or distal configuration. A male user 14 is depicted wearing the brief 46 and a urine collection pouch 16 is depicted in relation to the penis 18 and a breathable, tubular material 20 that aid in the placement and retention of the penis 18. In this configuration, that breathable, tubular material 20 is depicted as being located adjacent to, and separate from, the brief 46, and having a point of attachment 50, and central portion 52 that is generally cylindrical in shape to adapt to the shaft of the penis 18, and a terminal portion 54 that is depicted as having a double layer of material, in this case the same material as the brief 46. The breathable, tubular material 20 does not need to be made separately and attached to the brief 46. The pouch 16 is depicted having an absorbent material 56, which is within hydrophobic and watertight layers 58a and 58b. In operation, the breathable, tubular material 20 is first positioned in a rolled-up configuration, the penis head 18 is inserted into the opening 60 of the pouch 16, and the breathable, tubular material 20 can be rolled-on to the penis shaft. The pouch 16 will generally be shaped or elasticated to take into account the location of the testicles 61 to increase comfort during use of the brief 46. In this figure, the absorbent material 56 is shown both above, in-front of, and below the penis 18, between the legs and even upwardly and behind the buttocks. Also depicted is a channel or deflector 62, that directs the urine away from the penis and toward the absorbent material 56.

Figure 2D:
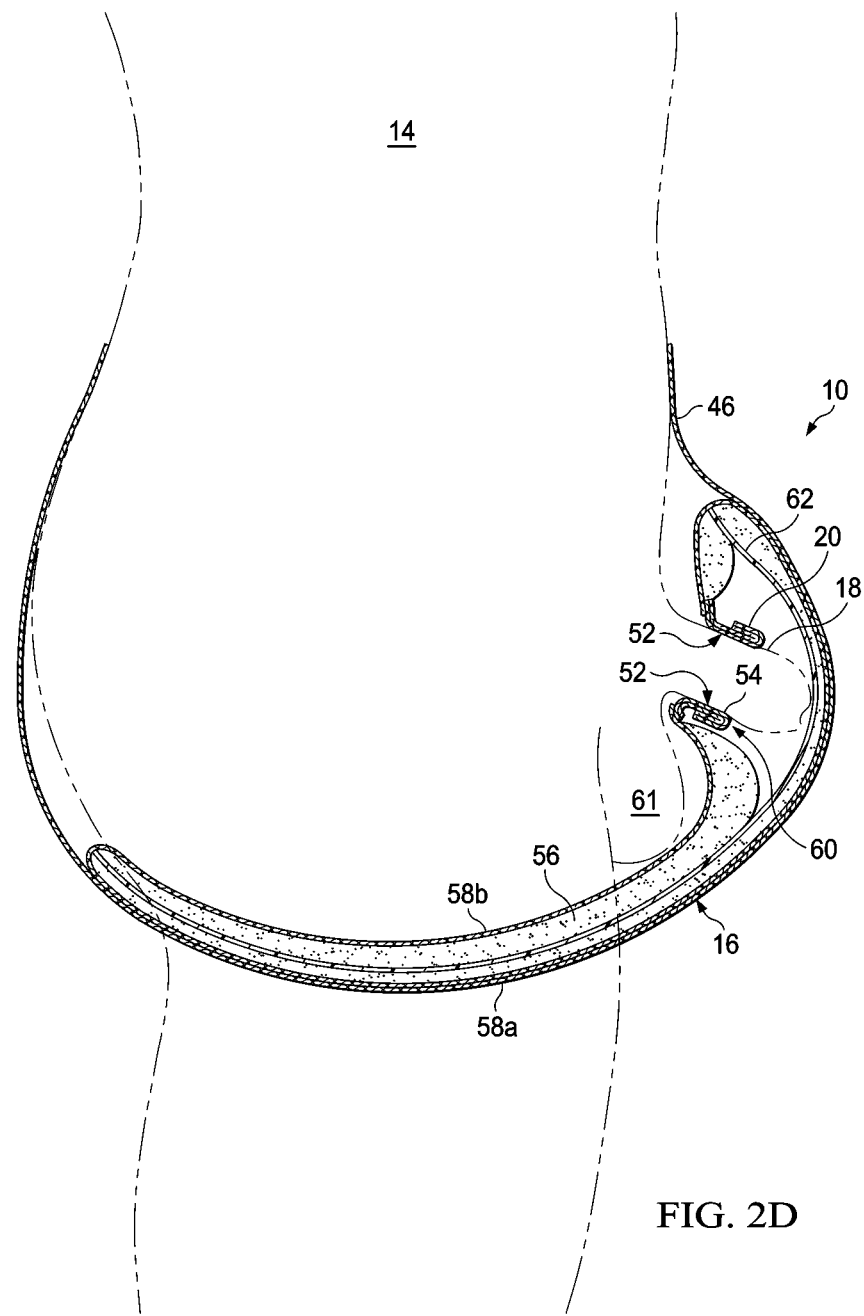
FIG. 2D is a detailed cross-sectional side view of the urine collection and male incontinence device of the present invention used in conjunction with a brief underwear with an outward or proximal configuration.

FIG. 2D is a detailed cross-sectional side view of the urine collection and male incontinence device of the present invention used in conjunction with a brief underwear 46 with an outward or proximal configuration. The breathable, tubular material 20 and showing the details of an outward or proximal configuration. A male user 14 is depicted wearing the boxer or garment 12 and a urine collection pouch 16 is depicted in relation to the penis 18 and a breathable, tubular material 20 that aid in the placement and retention of the penis 18. In this configuration, that breathable, tubular material 20 is depicted as being located adjacent to, and separate from, the brief 46, and having a point of attachment 50, and central portion 52 that is generally cylindrical in shape to adapt to the shaft of the penis 18, and a terminal portion 54 that is depicted as having a double layer of material, in this case the same material as the brief 46. The breathable, tubular material 20 does not need to be made separately and attached to the brief 46. The pouch 16 is depicted having an absorbent material 56, which is within hydrophobic and watertight layers 58a and 58b. In operation, the breathable, tubular material 20 is first positioned in a rolled-up configuration, the penis head 18 is inserted into the opening 60 of the pouch 16, and the breathable, tubular material 20 can be rolled-on to the penis shaft. The pouch 16 will generally be shaped or elasticated to take into account the location of the testicles 61 to increase comfort during use of the brief 46. In this configuration the penis 18 is slipped into the opening 60 and the shaft of the penis 18 is in contact with the central portion 52 of the breathable, tubular material 20. In this figure, the absorbent material 56 is shown both above, in-front of, and below the penis 18, between the legs and even upwardly and behind the buttocks. Also depicted is a channel or deflector 62, that directs the urine away from the penis and toward the absorbent material 56.

Figure 3:
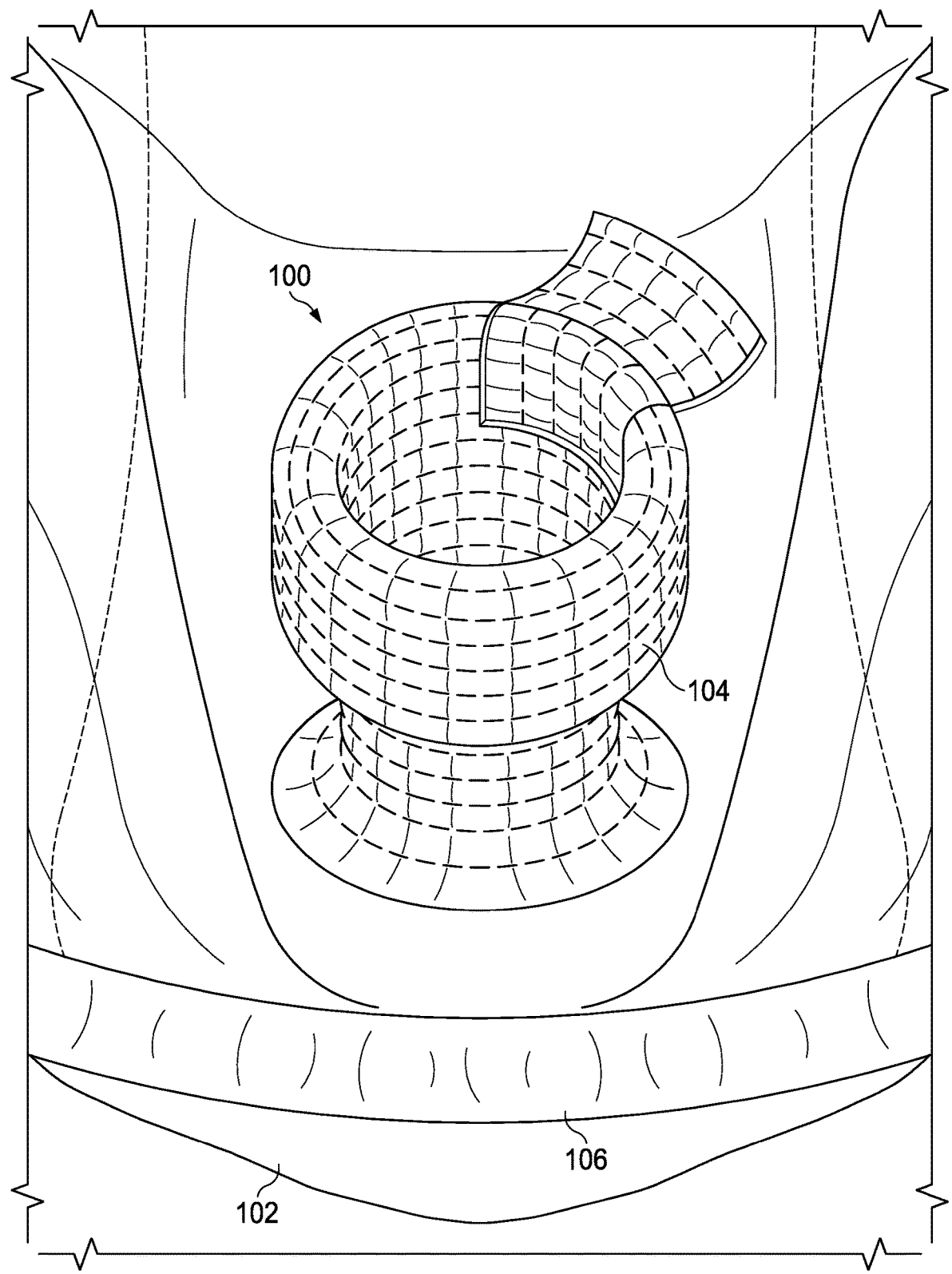
FIG. 3 shows an isometric, cut-out view of the elastic aperture adapted to allow a penis to extend into the chamber, wherein the elastic aperture is depicted as a tubular elasticated and bobbed material to aid in the placement and retention in place of the penis and is integral with the single-use, disposable diaper.

FIG. 3 shows an isometric, cut-out view of the elastic aperture 100 adapted to allow a penis to extend into a chamber 102, wherein the elastic aperture 100 is depicted as a tubular elasticated and bobbed material 104 to aid in the placement and retention in place of a penis (not depicted) and is integral with the single-use, disposable brief, boxer, or garment 106. In this isometric view, the bobbing and elastication is depicted integral with the elastic aperture 100, and will allow for limited breathing or passage the passage of air along a shaft of a penis to increase comfort, but importantly, to eliminate the stagnation of bacteria and fungal in an environment that promotes bacterial and fungal growth. It has been found that some breathing is important to eliminate bacteria that are obligate anaerobes. Non-limiting examples of obligate anaerobic bacterial genera include *Actinomyces, Bacteroides, Clostridium, Fusobacterium, Peptostreptococcus, Porphyromonas, Prevotella, Propionibacterium*, and *Veillonella*.

Figure 4:
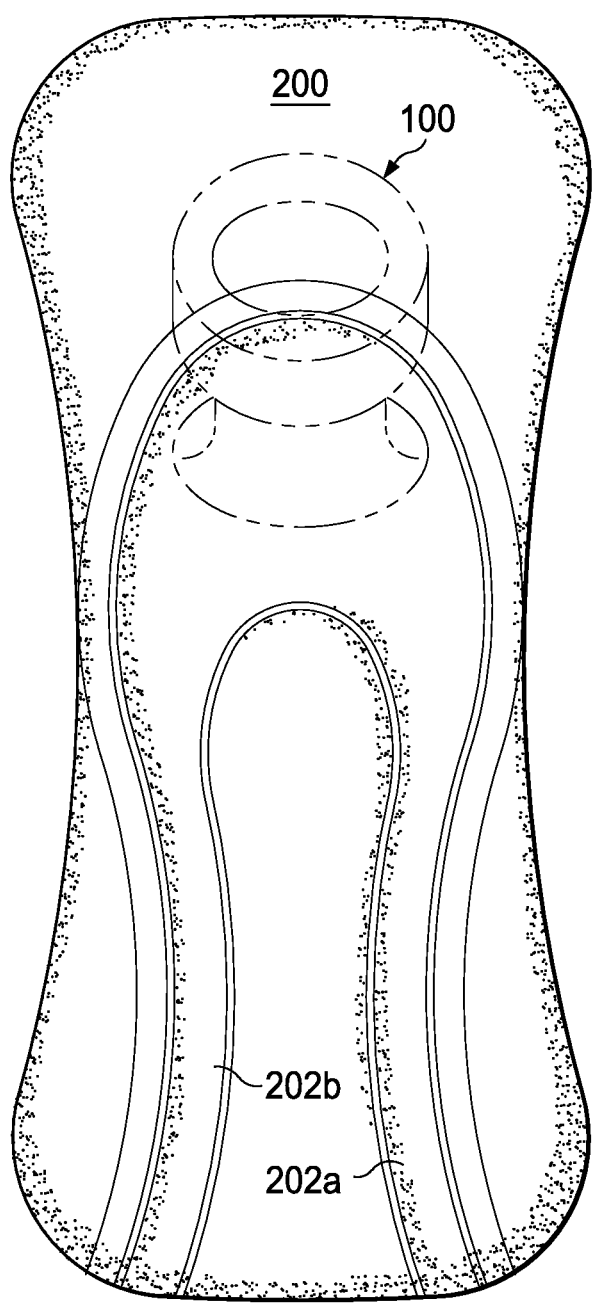
FIG. 4 shows a side, cut-out view of the elastic aperture adapted to allow a penis to extend into the urine collection and male incontinence device or pouch that can be used in conjunction with existing underwear.

FIG. 4 shows a side, cut-out view of the elastic aperture 100 adapted to allow a penis to extend into the urine collection and male incontinence device or pouch 200 that can be used in conjunction with existing underwear. In this configuration, the urine collection and male incontinence device or pouch 200 is a standalone device or pouch that is separate from an existing underwear, but configured to fit within the underwear, that is, between the underwear and the make user. In this configuration, the urine collection and male incontinence device or pouch 200 is depicted with channels 202a, 202b, that are shaped to direct urine that enters from the elastic aperture 100 toward an absorbent material (not depicted), to that the urine is directed away from the penis.

Figure 5A:
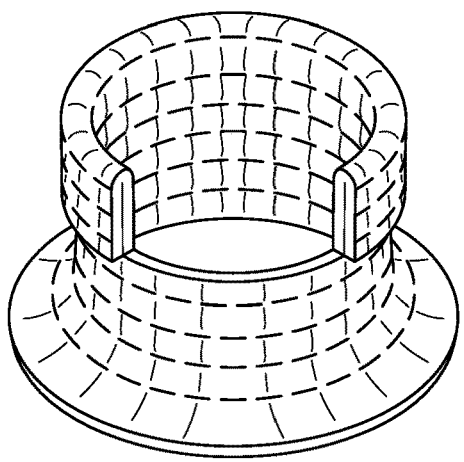
FIGS. 5A to 5F show various embodiments of patterns or features formed into the elastic aperture adapted to allow a penis to extend into the urine collection and male incontinence device or pouch.
Figure 5B:
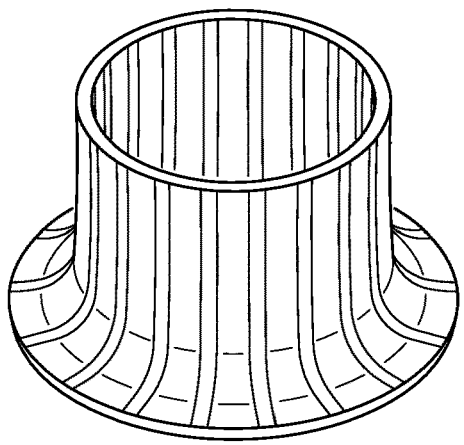
Figure 5C:
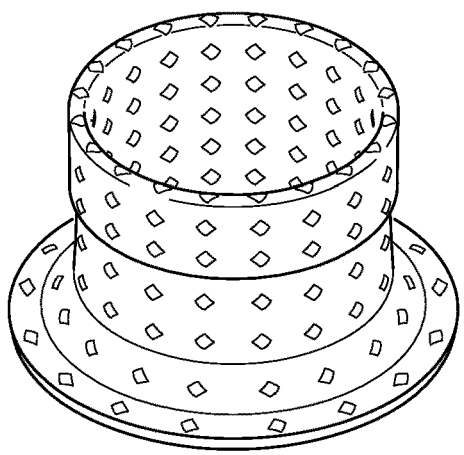
Figure 5D:
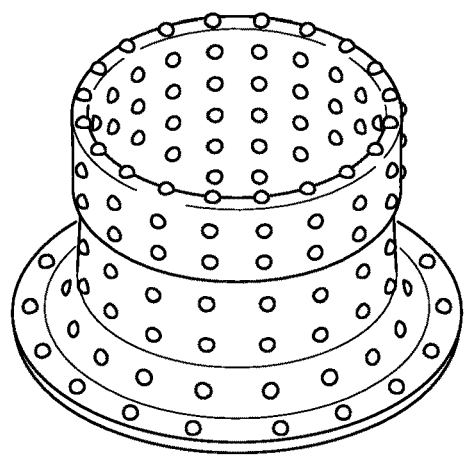
Figure 5E:
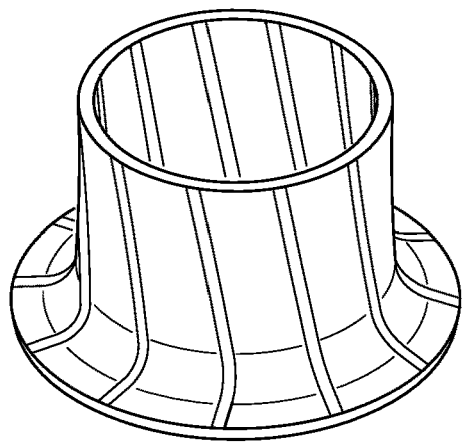
Figure 5F:
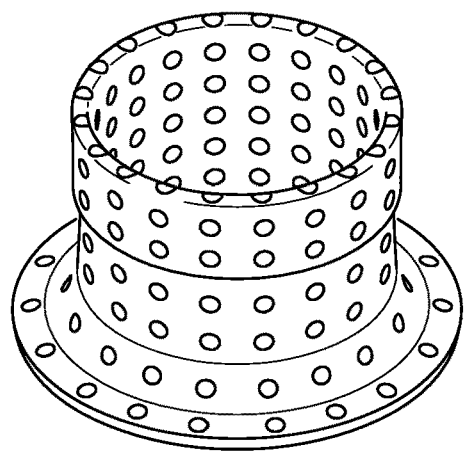

FIGS. 5A to 5F show various non-limiting embodiments of patterns or features formed into the elastic aperture adapted to allow a penis to extend into the urine collection and male incontinence device or pouch. Specifically, FIG. 5A shows an embodiment of the breathable, tubular material in which a stitched later is depicted with a cross-sectional cut-out that shows that the breathable, tubular material folds over at the end forming a double-walled or double-layer end. By contrast, FIG. 5B shows an embodiment that comprises grooves that are formed into a single layer of the material, thereby providing for the breathable, tubular material. FIG. 5C shows another embodiment of the breathable, tubular material in which a pattern (depicted here as a diamond pattern) can be embossed, punched, printed, stamped or formed in such a way to provide a breathable, tubular material. In this embodiment, there is also a fold-over, however, the skilled artisan will recognize that for each of these embodiments the material can be a single layer, a double layer, with or without a fold-over. FIG. 5D shows an embodiment in which raised bumps or protrusions are depicted (shown as generally spherical but any shape could be used), again with the optional fold-over. In FIG. 5E, a single layer version is depicted that differs from FIG. 5B in that the grooves are diagonal (and in certain embodiments may also include one or more combinations of perpendicular and one or more diagonal grooves or striations). Finally, FIG. 5F shows another non-limiting embodiment that is the opposite of FIG. 5D in that instead of bumps, spherical indentations, which, again, can have any shape. In certain embodiments, the grooves, bumps, indentations, stitching, etc., may be located on one side, the other side, or both sides of the breathable, tubular material.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A male incontinence collection container shaped and integral with a boxer or a brief, comprising:
    an inner layer and an outer layer joined together to form at least a front portion of a waistband of the boxer or brief, the inner layer configured for direct contact with a body of a user, the inner layer and the outer layer enclosing a chamber therebetween, the chamber extending from a lower abdomen of the user through an entire length of a crotch region of the user;
    wherein the chamber includes an aperture formed through the inner layer to allow a penis to be in fluid communication with the chamber, wherein the aperture comprises a tubular structure configured to roll outwardly from the chamber over a corona of the penis to a neck of the penis to aid in the placement and retention of the penis, wherein the tubular structure comprising an elasticated, hydrophobic, and breathable material that has protrusions, indentations, or stitching, and is formed such that the tubular structure permits gas to traverse from an outside environment into and out of the chamber;
    an absorbent material disposed in the chamber, the absorbent material configured to convert urine to gel upon absorbing the urine received through the aperture into the chamber; and
    a deflector layer disposed within the chamber for channeling urine into the absorbent material, the deflector layer extending along a front portion of the chamber and separating the absorbent material from the aperture;
    wherein the inner and outer layers are formed of a hydrophobic material.

2. The container of claim 1, wherein the chamber is integral with the brief, wherein the absorbent material in the chamber is positioned down a front of a groin and in an area between the legs of the user, wherein the absorbent material is made from a non-woven hydrophilic material selected from cellulose, modified-cellulose, linen, cotton, rayon fiber, viscose fiber, cotton fiber, lyocell fiber, or mixtures thereof, or wherein the chamber is shaped to contour around a leg portion of elongated briefs to evenly distribute the liquid throughout the chamber to reduce or eliminate bulging of the brief.

3. The container of claim 1, wherein the male incontinence collection container is integral with a brief or boxer and the brief or boxer is disposable, and the container is single use.

4. The container of claim 1, wherein the hydrophobic layer comprises polyester/polyethylene terephthalate (PET), polyamide 6 (PA6), polyamide 66 (PA66), nylon 6, nylon 66, polypropylene (PP), or polyolefin, modacrylic or copolymer thereof, a fluoropolymer selected from polytetrafluoroethylene (PTFE), perfluoroalkoxy polymer (PFA), or fluorinated ethylene-propylene (FEP), polypropylene, polyethyleneterephthalate, polybutyleneterephthalate, poly(trimethylene terephthalate), polylactide, nylon, polyacrylonitrile, polybenzimidazole, fluoropolymer, a copolymers thereof, or a combination thereof.

5. The container of claim 1, where the inner layer and/or the outer layer is channeled toward the absorbent material, and optionally the inner layer and/or the outer layer further comprises a channel, groove, or imprinting that channels urine toward the absorbent material in the chamber.

6. The container of claim 1, wherein the absorbent material comprises polybeads, a hydrogel forming polymer, a polymer comprising one or more saturated amines and/or saturated polyamines selected from (mono, di and poly) aminoalkanes, (mono, di and poly)aminopolyethers, allylamine, alkyl(meth)allylamines, e.g., methyl allylamine, methyl methallylamine, ethyl methallylamine, and ethyl allylamine; methyl-, ethyl-, propyl- and butylamine, diallylamine, dimethallylamine, aniline, ethylenediamine, diethylenetriamine, hexamethylenediamine, trimethylhexamethylenediamine, neopentane diamine, 1,2-propylenediamine, 4,7-dioxadecane-1,10-diamine, 4,9-dioxadodecane-1,12-diamine, polyether diamines, polyalkylene glycol diamines, 3-amino-1-methylaminopropane, bis(3-aminopropyl)methylamine, isophorone diamine, 4,4'-diaminodicyclohexylmethane, 1-(2-aminoethyl)piperazine, o-, m-, or p-phenylenediamine, 4,4'-diaminodiphenyimethane, 1,4-diaminoanthraquinone, 2,4,6-triamino-1,3,5-triazine, aminopyridine, glucosamine, or mixtures thereof.

* * * * *